(12) United States Patent
Bender et al.

(10) Patent No.: US 9,345,725 B2
(45) Date of Patent: May 24, 2016

(54) PHARMACEUTICAL FORMULATIONS OF GALLIUM SALTS

(75) Inventors: Lewis Bender, Redding, CT (US); Bavani Shankar, Nanuet, NY (US); Catherina O'Shaughnessy, Cootehill (IE)

(73) Assignee: EMISPHERE TECHNOLOGIES, INC., Roseland, NJ (US)

( * ) Notice: Subject to any disclaimer, the term of this patent is extended or adjusted under 35 U.S.C. 154(b) by 1545 days.

(21) Appl. No.: 11/722,618

(22) PCT Filed: Dec. 29, 2005

(86) PCT No.: PCT/US2005/047603
§ 371 (c)(1),
(2), (4) Date: Sep. 7, 2007

(87) PCT Pub. No.: WO2006/072070
PCT Pub. Date: Jul. 6, 2006

(65) Prior Publication Data
US 2009/0123562 A1 May 14, 2009

Related U.S. Application Data

(60) Provisional application No. 60/640,739, filed on Dec. 29, 2004, provisional application No. 60/677,533, filed on May 3, 2005.

(51) Int. Cl.
*A61K 33/24* (2006.01)
*A61K 31/195* (2006.01)
*A61K 31/28* (2006.01)
*A61K 9/00* (2006.01)
*A61K 31/351* (2006.01)
*A61K 47/12* (2006.01)
*A61K 47/18* (2006.01)

(52) U.S. Cl.
CPC .............. *A61K 33/24* (2013.01); *A61K 9/0019* (2013.01); *A61K 9/0095* (2013.01); *A61K 31/195* (2013.01); *A61K 31/351* (2013.01); *A61K 47/12* (2013.01); *A61K 47/183* (2013.01)

(58) Field of Classification Search
CPC . A61K 31/192; A61K 33/24; A61K 2300/00; A61K 47/183
See application file for complete search history.

(56) References Cited

U.S. PATENT DOCUMENTS

| | | | |
|---|---|---|---|
| 4,529,593 A | 7/1985 | Warrell, Jr. et al. | |
| 4,704,277 A | 11/1987 | Bockman et al. | |
| 5,196,412 A * | 3/1993 | Bradley et al. | 514/184 |
| 5,650,386 A * | 7/1997 | Leone-Bay et al. | 424/85.2 |
| 5,773,647 A * | 6/1998 | Leone-Bay et al. | 562/444 |
| 5,804,688 A * | 9/1998 | Leone-Bay et al. | 562/444 |
| 5,866,536 A | 2/1999 | Leone-Bay et al. | |
| 5,876,710 A * | 3/1999 | Leone-Bay et al. | 424/85.1 |
| 5,879,681 A * | 3/1999 | Leone-Bay et al. | 424/85.1 |
| 5,990,166 A * | 11/1999 | Leone-Bay et al. | 514/563 |
| 6,071,510 A * | 6/2000 | Leone-Bay et al. | 424/85.2 |
| 6,087,354 A * | 7/2000 | Bernstein | 514/184 |
| 6,313,088 B1 * | 11/2001 | Leone-Bay et al. | 424/85.4 |
| 6,344,213 B1 * | 2/2002 | Leone-Bay et al. | 424/451 |
| 6,693,208 B2 * | 2/2004 | Gscheidner et al. | 554/1 |
| 6,960,355 B2 * | 11/2005 | Leone-Bay et al. | 424/451 |
| 6,991,798 B1 * | 1/2006 | Gschneidner et al. | 424/400 |
| 7,186,414 B2 * | 3/2007 | Gschneidner et al. | 424/400 |
| 7,351,741 B2 * | 4/2008 | Weidner et al. | 514/557 |
| 7,354,952 B2 * | 4/2008 | Julian | 514/492 |
| 7,495,030 B2 * | 2/2009 | Gschneidner | 514/557 |
| 7,744,910 B2 * | 6/2010 | Gschneidner et al. | 424/400 |
| 2002/0065255 A1 * | 5/2002 | Bay et al. | 514/166 |
| 2005/0277621 A1 * | 12/2005 | Gschneidner | 514/89 |

FOREIGN PATENT DOCUMENTS

| | | | |
|---|---|---|---|
| WO | WO-9736480 A1 | 10/1997 | |
| WO | WO-0059863 A1 | 10/2000 | |
| WO | WO 02/02509 A1 * | 1/2002 | |
| WO | 02/070438 A1 | 9/2002 | |
| WO | WO-03045331 A2 | 6/2003 | |
| WO | WO-03057650 A2 | 7/2003 | |

OTHER PUBLICATIONS

The Merck Index (12th Edition, 1996, pp. 737-738, Entry 4364).*
Bernstein Lawrence R et al.: "Chemistry and Pharmacokinetics of gallium maltolate, a compound with high oral gallium bioavailability" Metal-Based Drugs, Freund Publishing House, Tel Aviv, IL LNKD-DOI: 10.1155/MBD. 2000.33, vol. 7, No. 1, Jan. 1, 2000, pp. 33-47 XP002566955 ISSN: 0793-0291.

* cited by examiner

*Primary Examiner* — James D Anderson
(74) *Attorney, Agent, or Firm* — Blank Rome LLP

(57) ABSTRACT

The present invention relates to pharmaceutical formulations containing a pharmaceutically acceptable gallium salt (such as gallium nitrate), a delivery agent, and optionally, one or more chemotherapeutic agents and/or adjunctive chemotherapeutic agents.

11 Claims, 1 Drawing Sheet

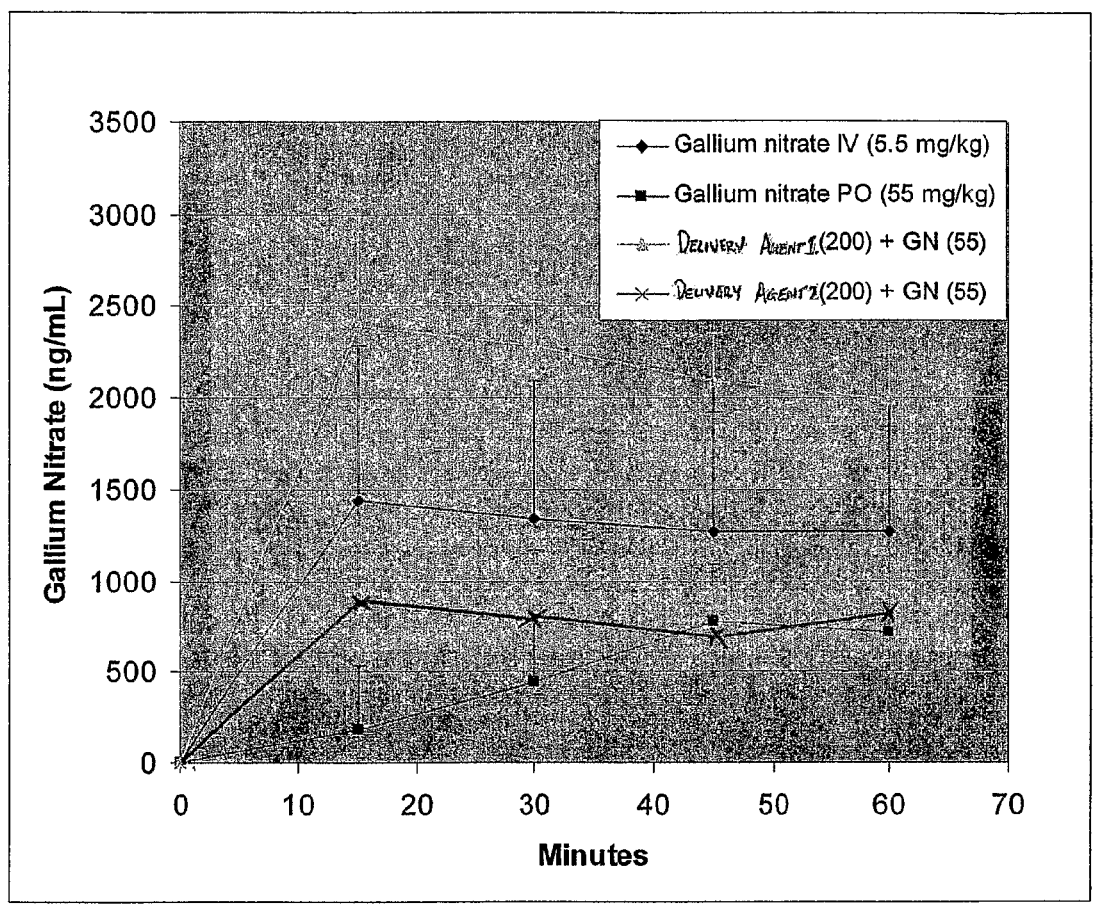

PHARMACEUTICAL FORMULATIONS OF GALLIUM SALTS

This application is a national phase of International Application No. PCT/US2005/047603, filed Dec. 29, 2005, which claims the benefit of U.S. Provisional Application No. 60/640,739 filed Dec. 29, 2004 and U.S. Provisional Application No. 60/677,533 filed May 3, 2005. Each of these applications is incorporated by reference in its entirety.

FIELD OF THE INVENTION

The present invention relates to pharmaceutical formulations containing a pharmaceutically acceptable gallium salt (such as gallium nitrate), a delivery agent, and optionally, one or more chemotherapeutic agents and/or adjunctive chemotherapeutic agents.

BACKGROUND OF THE INVENTION

Conventional means for delivering drugs are often severely limited by biological, chemical, and physical barriers. Typically, these barriers are imposed by the environment through which delivery occurs, the environment of the target for delivery, and/or the target itself. Examples of physical barriers include the skin, lipid bi-layers and various organ membranes that are relatively impermeable to certain drugs but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many drugs would be the route of choice for administration if not for biological, chemical, and physical barriers that prevent, restrict or reduce the passage of drugs. Among the numerous agents in this category are gallium salts.

U.S. Pat. No. 4,529,593 discloses a method of preventing or treating a disorder associate with accelerated loss of calcium from bone in a human individual by administering to the individual a pharmaceutically acceptable gallium compound, such as gallium nitrate.

U.S. Pat. No. 4,704,277 discloses a method of increasing bone growth, decreasing hydroxyapatite solubility, increasing the size and/or the perfection of hydroxyapatite crystals in bone, and/or increasing the tensile strength of bone by administering to an individual a pharmaceutically acceptable gallium compound, such as gallium nitrate.

Gallium nitrate is currently marketed as Ganite™, an intravenous injection, for the treatment of clearly symptomatic cancer-related hypercalcemia that has not responded to adequate hydration. Gallium nitrate is not currently available as an oral formulation due to its poor oral bioavailability. According to the FDA approved labeling for Ganite™, gallium nitrate exerts a hypocalcemic effect by inhibiting calcium resorption from bone, possibly by reducing increased bone turnover.

Additionally, according to the FDA approved labeling for Ganite™, hypercalcemia is a common problem in hospitalized patients with malignancy. It may affect 10-20% of patients with cancer. Different types of malignancy seem to vary in their propensity to cause hypercalcemia. A higher incidence of hypercalcemia has been observed in patients with non-small cell lung cancer, breast cancer, multiple myeloma, kidney cancer, and cancer of head and neck. Hypercalcemia of malignancy seems to result from an imbalance between the net resorption of bone and urinary excretion of calcium. Patients with extensive osteolytic bone metastases frequently develop hypercalcemia. This type of hypercalcemia is common with primary breast cancer. Some of these patients have been reported to have increased renal tubular calcium resorption. Breast cancer cells have been reported to produce several potential bone-resorbing factors which stimulate the local osteoclast activity. Humoral hypercalcemia is common with the solid tumors of the lung, head and neck, kidney, and ovaries. Systemic factors (e.g., PTH-rP) produced either by the tumor or host cells have been implicated for the altered calcium fluxes between the extracellular fluid, the kidney, and the skeleton. About 30% of patients with myeloma develop hypercalcemia associated with extensive osteolytic lesions and impaired glomerular filtration. Myeloma cells have been reported to produce local factors that stimulate adjacent osteoclasts. Hypercalcemia may produce a spectrum of signs and symptoms including: anorexia, lethargy, fatigue, nausea, vomiting, constipation, polyuria, dehydration, renal insufficiency, impaired mental status, coma, EKG abnormalities and cardiac arrest.

One type of hypercalcemia, "Non-PTH-Mediated Hypercalcemia", is theorized to result from an increase in osteoclastic activity. While malignant disorders are a common cause of this type of hypercalcemia, it may also be due to other causes. Granulomatous disorders with high levels of calcitriol may be found in patients with sarcoidosis, berylliosis, tuberculosis, leprosy, coccidioidomycosis, and histoplasmosis. Iatrogenic disorders of calcium levels may increase secondary to the ingestion of many medications (e.g. thiazide diuretics, calcium carbonate, hypervitaminosis D, hypervitaminosis A, lithium, milk-alkali syndrome and thephylline toxicity). Chronic renal failure, post transplant states and hemodialysis may also cause hypercalcemia.

Hypercalcemia may also result from Primary Hyperparathyroidiam. Plasma calcium is maintained within the reference range by a complex interplay of 3 major hormones, parathyroid hormone (PTH), 1,25-dihydroxyvitamin D (ie, calcitriol), and calcitonin. These 3 hormones act primarily at bone, kidney, and small intestine sites to maintain appropriate calcium levels. In most primary hyperparathyroidism cases, the calcium elevation is caused by increased intestinal calcium absorption. This is mediated by the PTH-induced calcitriol synthesis that enhances calcium absorption. The increase in serum calcium results in an increase in calcium filtration at the kidney. Because of PTH-mediated absorption of calcium at the distal tubule, less calcium is excreted than might be expected. Generally, in PTH-mediated hypercalcemia, bones do not play an active role because most of the PTH-mediated osteoclast activity that breaks down bone is offset by hypercalcemic-induced bone deposition.

A goal of treatment is to stabilize and reduce the calcium level, increase urinary calcium excretion, inhibit osteoclast activity in the bone, and treat underlying causes when possible.

There is a need for improved oral delivery systems for gallium salts which provide sufficient bioavailability to treat hypercalcemia.

SUMMARY OF THE INVENTION

The present invention is a pharmaceutical formulation comprising a pharmaceutically acceptable gallium salt, preferably gallium nitrate, and at least one delivery agent. The delivery agent facilitates the delivery and increases the bioavailability of the gallium salt. A preferred gallium salt is gallium nitrate nonahydrate $(Ga(NO_3)_3 \cdot 9H_2O)$. Preferably, the pharmaceutical formulation is orally administered. The oral pharmaceutical formulations of the present invention preferably only require once-a-day administration. More frequent administrations with or without fluids and loop diuretics is also contemplated to be within the scope of the present invention.

A preferred embodiment of the present invention is a sustained release oral pharmaceutical formulation of a pharmaceutically acceptable gallium salt, preferably gallium nitrate, and at least one delivery agent. Because the anticalcium effect of gallium salts is schedule related (i.e., prolonged exposure to lower concentrations produces greater inhibition of bone resorption than short treatment with high doses), the sustained release oral formulations of the present invention may provide improved efficacy. Sustained release formulations may also reduce undesirable side effects resulting from rapid absorption of the gallium salt, such as nausea, vomiting, and an increased risk of renal insufficiency.

Another preferred embodiment is an oral pharmaceutical formulation comprising a pharmaceutically acceptable gallium salt, preferably gallium nitrate, and at least one delivery agent which provides, upon ingestion to a human, one or more of the following:

(a) plasma gallium concentrations of about 0.1 to about 5 μg/ml or about 0.9 to about 2.0 μg/ml, (b) average steady state plasma levels of gallium from about 1000 to about 2500 ng/ml, or (c) a decrease in serum calcium (corrected for albumin) of at least 2.0 mg/dl in a human with hypercalcemia (such as cancer-related hypercalcemia).

Another embodiment is a method of treating or preventing hypercalcemia in a mammal (e.g., a human) in need thereof by administering to the mammal an effective amount of the pharmaceutical formulation of the present invention. For example, the pharmaceutical formulation may be administered to treat cancer-related hypercalcemia. In a preferred embodiment, the mammal is a human suffering from hypercalcemia and has a serum calcium (corrected for albumin) of less than 12 mg/dL.

Yet another embodiment is a method of treating or preventing a disorder associated with excessive (or accelerated) loss of calcium from bone in a mammal (such as a human) by administering to the mammal an effective amount of the pharmaceutical formulation of the present invention. Such disorders include, but are not limited to, hypercalcemia, osteopenia, osteoporosis, bone destruction due to metastasis from malignant tumors, hyperparathyroidism, renal disease, iatrogenic disease (including drug-induced diseases), and periodontal disease.

Yet another embodiment is a method of inhibiting resorption or release of calcium from bone in a mammal (such as a human) with hypercalcemia, bone fragility, or other disorder associated with abnormally increased calcium resorption or release by administering to the mammal an effective amount of the pharmaceutical formulation of the present invention.

Yet another embodiment is a method of treating bone pain due to excessive (or accelerated) loss of calcium from bone in a mammal (e.g., human) by administering to the mammal an effective amount of the pharmaceutical formulation of the present invention.

Yet another embodiment is a method of preventing bone fractures due to excessive (or accelerated) loss of calcium from bone in a mammal (e.g., human) by administering to the mammal an effective amount of the pharmaceutical formulation of the present invention.

Yet another embodiment is a method of increasing bone growth, decreasing hydroxyapatite solubility, increasing the size and/or perfection of hydroxyapatite crystals in bone, and/or increasing the tensile strength of bone in a mammal (e.g., human) by administering to the mammal an effective amount of the pharmaceutical formulation of the present invention.

Yet another embodiment is a method of increasing calcium accretion in bone tissue and/or decreasing bone resorption in a mammal (e.g., human) by administering to the mammal an effective amount of the pharmaceutical formulation of the present invention.

Any of the aforementioned methods may be augmented by administration of fluids (such as water), loop diuretics, a chemotherapeutic agent, and an adjunctive chemotherapeutic agent (such as filgrastim and erythropoietin), or any combination of the foregoing.

Yet another embodiment is a method for administering a gallium salt, such as gallium nitrate, to a mammal (e.g., a human) in need thereof by administering to the mammal the pharmaceutical formulation of the present invention.

Yet another embodiment is a method of preparing a pharmaceutical formulation of the present invention by mixing at least one delivery agent, at least one pharmaceutically acceptable gallium salt, and, optionally, one or more pharmaceutically acceptable additives or excipients.

BRIEF DESCRIPTION OF THE DRAWINGS

FIG. 1 shows the plasma gallium concentrations in rats following oral administration of (1) gallium nitrate (55 mg/kg) with disodium SNAC ("Delivery Agent 1"), (2) gallium nitrate (55 mg/kg) with the disodium salt of compound 2 of International Publication No. WO 03/045306 (8-(2-hydroxyphenoxy)octyldiethanolamine) ("Delivery Agent 2"), or (3) gallium nitrate (55 mg/kg) without a delivery agent, or (IV) intravenous administration of gallium nitrate (5.5 mg/kg).

DETAILED DESCRIPTION OF THE INVENTION

Definitions

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the formulations can mean a range of up to 10%, preferably up to 5%.

The terms "alkyl", "alkenyl", "alkoxy", "alkylene", "alkenylene", "alkyl(arylene)", and "aryl(alkylene)" include, but are not limited to, linear and branched alkyl, alkenyl, alkoxy, alkylene, alkenylene, alkyl(arylene), and aryl(alkylene) groups, respectively.

The phrase "pharmaceutically acceptable" refers to compounds or compositions that are physiologically tolerable and do not typically produce an allergic or similar untoward reaction, such as gastric upset, dizziness and the like, when administered to a mammal.

An "effective amount of gallium salt" or "effective amount of gallium nitrate" means the amount of gallium salt or salts, or gallium nitrate (including its solvates, active metabolites, prodrugs, or racemates or enantiomers thereof (assuming the salt has a chiral center)) that, when administered to a mammal for treating or preventing a state, disorder or condition is sufficient to effect such treatment or prevention. The "effective amount" will vary depending on the active ingredient, the state, disorder, or condition to be treated and its severity, and the age, weight, physical condition and responsiveness of the mammal to be treated. According to one embodiment of the present invention, a therapeutically effective amount of a gallium salt is an amount effective to treat any one of the above mentioned disorders. The gallium salt may be augmented with a second medication (such as a loop diuretic, a chemotherapeutic agent, or adjunctive chemotherapeutic agent to treat any of the aforementioned disorders, such as malignancies and hypercalcemia.

An "effective amount of delivery agent" refers to an amount of the delivery agent that promotes the absorption of a desired amount of the gallium salt from, for example, the gastrointestinal tract.

An "effective amount of the pharmaceutical formulation" is an amount of the pharmaceutical formulation described which is effective to treat or prevent a condition in a subject to whom it is administered over some period of time, e.g., provides a therapeutic effect during a desired dosing interval. Generally, an effective amount of the pharmaceutical formulation includes amounts of gallium salt and at least one delivery agent to treat or prevent the desired condition over a desired period of time (i.e., an effective amount of delivery agent and an effective amount of gallium salt).

As used herein, the term "treat" includes one or more of the following:

(a) arresting, delaying the onset (i.e., the period prior to clinical manifestation of a disorder) and/or reducing the risk of developing or worsening a disorder;

(b) relieving or alleviating at least one symptom of a disorder in a mammal, including for example, hypercalcemia; or (c) relieving or alleviating the intensity and/or duration of a manifestation of a disorder experienced by a mammal including, but not limited to, those which are in response to a given stimulus (e.g., pressure, tissue injury or cold temperature). The term "treat" also includes prophylactically preventing, curing, healing, alleviating, relieving, altering, remedying, ameliorating, improving, or affecting a condition (e.g., a disease), the symptoms of the condition, or the predisposition toward the condition.

The term "sustained release" as used herein refers to the release of an active ingredient over an extended period of time leading to lower peak plasma concentrations and a prolonged $T_{max}$ as compared to "immediate release" formulations of the same active ingredient.

The term "bioavailability" refers to the rate and extent to which the active ingredient (gallium salt) or active moiety is absorbed from a drug product and becomes systematically available.

The term "polymorph" refers to crystallographically distinct forms of a substance.

The term "hydrate" as used herein includes, but is not limited to, (i) a substance containing water combined in the molecular form and (ii) a crystalline substance containing one or more molecules of water of crystallization or a crystalline material containing free water.

The term "SNAC" as used herein refers to N-(8-[2-hydroxybenzoyl]-amino) caprylic acid and pharmaceutically acceptable salts thereof, including its monosodium and disodium salt. The term "SNAC free acid" refers to N-(8-[2-hydroxybenzoyl]-amino) caprylic acid. Unless otherwise noted, the term "SNAC" refers to all forms of SNAC, including all amorphous and polymorphic forms of SNAC, such as SNAC trihydrate and those described in U.S. Ser. Nos. 60/619,418 and 60/569,476, both of which are hereby incorporated by reference. The term "SNAC trihydrate" as used herein refers to a crystalline form of SNAC in which three molecules of water are associated with each molecule of SNAC. SNAC can be prepared by the procedures described in U.S. Pat. No. 5,650,386 and International Publication Nos. WO00/46182 and WO00/59863.

The term "SNAD" as used herein refers to N-(8-[2-hydroxybenzoyl]-amino) decanoic acid and pharmaceutically acceptable salts thereof, including its monosodium salt. Unless otherwise noted, the term "SNAD" refers to all forms of SNAD, including all amorphous and polymorphic forms of SNAD.

The term "4-CNAB" as used herein refers to 4-[(4-chloro-2-hydroxy-benzoyl)amino]butanoic acid (also known as 4-[(2-hydroxy-4-chlorobenzoyl)amino]butanoate) and pharmaceutically acceptable salts thereof, including its sodium salt (e.g., monosodium salt). Unless otherwise noted, the term "4-CNAB" refers to all forms of 4-CNAB, including all amorphous and polymorphic forms of 4-CNAB. The term "sodium 4-CNAB" and "mono-sodium 4-CNAB" refer to monosodium 4-[(2-hydroxy-4-chlorobenzoyl)amino]butanoate, including anhydrous, monohydrate, and isopropanol solvates thereof and amorphous and polymorphic forms thereof (including those described in International Publication No. WO 03/057650 which is hereby incorporated by reference), unless otherwise indicated.

The term "solvate" as used herein includes, but is not limited to, a molecular or ionic complex of molecules or ions of a solvent with molecules or ions of a delivery agent or gallium salt.

The term "delivery agent" refers to any of the delivery agent compounds disclosed or incorporated by reference herein.

The term "adjunctive chemotherapeutic agent" includes agents which treat, alleviate, relieve, or amelliorate the side effects of chemotherapeutic agents. Such agents include those which modify blood cell growth and maturation. Examples of adjunctive chemotherapeutic agents include, but are not limited to, filgrastim and erythropoietin.

The term "gallium salt" includes gallium salt or salts, gallium complexes and active metabolites, prodrugs, racemates, enantiomers, and hydrates thereof.

The term "chemotherapeutic agent" includes any agent which treats, prevents, cures, heals, alleviates, relieves, alters, remedies, ameliorates, improves, or affects malignancies and their metastasis. Examples of such agents (also known as "antineoplastic agents") include, but are not limited to, prednisone, fluorouracil (e.g., 5-fluorouracil (5-FU)), anastrozole, bicalutamide, carboplatin, cisplatin, chlorambucil, docetaxel, doxorubicin, flutamide, interferon-alpha, letrozole, leuprolide, megestrol, mitomycin, paclitaxel, plicamycin (Mithracin™), tamoxifen, thiotepa, topotecan, valrubicin, vinvlastin, vincristine, and any combination of any of the foregoing.

The terms "2-OH—Ar" or "2-HO—Ar", as used in formulas 1 and 2 refers to an aryl group that is substituted with a hydroxy group at the 2 position.

Delivery Agent Compounds

Suitable delivery agents include those having the following structure and pharmaceutically acceptable salts thereof:

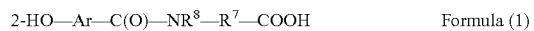

2-HO—Ar—C(O)—NR$^8$—R$^7$—COOH          Formula (1)

wherein

Ar is phenyl or naphthyl, optionally substituted with OH, halogen, $C_1$-$C_4$ alkyl, $C_1$-$C_4$ alkenyl, $C_1$-$C_4$ alkoxy or $C_1$-$C_4$ haloalkoxy;

$R^7$ is $C_4$-$C_{20}$ alkyl, $C_4$-$C_{20}$ alkenyl, phenyl, naphthyl, ($C_1$-$C_{10}$ alkyl)phenyl, ($C_1$-$C_{10}$ alkenyl)phenyl, ($C_1$-$C_{10}$ alkyl) naphthyl, ($C_1$-$C_{10}$ alkenyl) naphthyl, phenyl($C_1$-$C_{10}$ alkyl), phenyl($C_1$-$C_{10}$ alkenyl), naphthyl($C_1$-$C_{10}$ alkyl), or naphthyl ($C_1$-$C_{10}$ alkenyl);

R⁸ is hydrogen, $C_1$ to $C_4$ alkyl, $C_2$ to $C_4$ alkenyl, $C_1$ to $C_4$ alkoxy, $C_1$-$C_4$ or haloalkoxy;

R⁷ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, and —CO₂R⁹ or any combination thereof;

R⁹ is hydrogen, $C_1$ to $C_4$ alkyl or $C_2$ to $C_4$ alkenyl; and

R⁷ is optionally interrupted by oxygen, nitrogen, sulfur or any combination thereof; with the proviso that the compounds are not substituted with an amino group in the position alpha to the acid group or salts thereof.

According to one embodiment, Ar is substituted with a halogen.

Preferably, R⁷ is $C_4$-$C_{20}$ alkyl or phenyl($C_1$-$C_{10}$ alkyl). More preferably R⁷ is $C_5$-$C_{10}$ alkyl or phenyl($C_2$ alkyl). Most preferably, R⁷ is $C_7$-$C_8$ alkyl or phenyl($C_2$ alkyl).

Other suitable delivery agents include those having the following structure and pharmaceutically acceptable salts thereof:

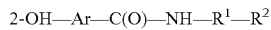

2-OH—Ar—C(O)—NH—R¹—R²   Formula (2)

wherein

Ar is phenyl or naphthyl;

Ar is optionally substituted with $C_1$-$C_4$ alkyl, $C_1$-$C_4$ alkoxy, $C_2$-$C_4$ alkenyl, $C_2$-$C_4$ alkynyl, aryl, aryloxy, a heterocyclic ring, $C_5$-$C_7$ carbocyclic ring, halogen, —OH, —SH, CO₂R⁶, —NR⁷R⁸, or —N⁺R⁷R⁸R⁹Y⁻;

(a) R¹ is $C_1$-$C_{16}$ alkylene, $C_2$-$C_{16}$ alkenylene, $C_2$-$C_{16}$ alkynylene, $C_6$-$C_{16}$ arylene, ($C_1$-$C_{16}$ alkyl)arylene, or aryl ($C_1$-$C_{16}$ alkylene);

R² is —NR³R⁴ or —N⁺R³R⁴R⁵Y⁻;

R³ and R⁴ are independently hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

R⁵ is independently hydrogen; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

(b) R¹, R², and R⁵ are as defined above; and

R³ and R⁴ are combined to form a 5, 6 or 7-membered heterocyclic ring; or 5, 6 or 7-membered heterocyclic ring substituted with a $C_1$-$C_6$ alkyl, $C_1$-$C_6$ alkoxy, aryl, aryloxy, oxo group or carbocyclic ring; or (c) R² and R⁵ are as defined above; and R¹ and R³ are combined to form a 5, 6 or 7-membered heterocyclic ring; or 5, 6 or 7-membered heterocyclic ring substituted with a $C_1$-$C_6$ alkyl, alkoxy, aryl, aryloxy, or oxo group or carbocyclic ring;

R⁴ is hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

R⁶ is hydrogen; $C_1$-$C_4$ alkyl; $C_1$-$C_4$ alkyl substituted halogen or —OH; $C_2$-$C_4$ alkenyl; or $C_2$-$C_4$ alkenyl substituted halogen or —OH;

R⁷, R⁸, and R⁹ are independently hydrogen; oxygen; $C_1$-$C_4$ alkyl; $C_1$-$C_4$ alkyl substituted with halogen or —OH; $C_2$-$C_4$ alkenyl; or $C_2$-$C_4$ alkenyl substituted with halogen or —OH; and Y is halogen, hydroxide, sulfate, nitrate, phosphate, alkoxy, perchlorate, tetrafluoroborate, or carboxylate. A non-limiting example of a suitable carboxylate is acetate.

The term "substituted" as used herein with respect to the compounds of formula (2) includes, but is not limited to, hydroxyl and halogen.

In one embodiment, Ar is unsubstituted phenyl or phenyl substituted with one or more of $C_1$-$C_4$ alkyl, $C_1$-$C_4$ alkoxy, or halogen. More preferably, Ar is a phenyl substituted with methoxy, Cl, F or Br, and even more preferably, Ar is a phenyl substituted with Cl.

In another embodiment, R¹ is $C_1$-$C_{12}$ alkyl, $C_2$-$C_8$ alkyl, $C_2$-$C_6$ alkyl, or $C_6$ alkyl.

In another embodiment, R³ and R⁴ are independently H or $C_1$-$C_2$ alkyl; or further R³ and R⁴ are not both H; or further R³ and R⁴ are independently methyl or ethyl; and more preferably R³ and R⁴ are both methyl.

Other suitable delivery agents include those having the following structure and pharmaceutically acceptable salts thereof:

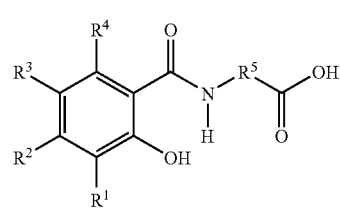

Formula (3)

wherein

R¹, R², R³, and R⁴ are independently hydrogen, —OH, —NR⁶R⁷, halogen, $C_1$-$C_4$ alkyl, or $C_1$-$C_4$ alkoxy;

R⁵ is a substituted or unsubstituted $C_2$-$C_{16}$ alkylene, substituted or unsubstituted $C_2$-$C_{16}$ alkenylene, substituted or unsubstituted $C_1$-$C_{12}$ alkyl(arylene), or substituted or unsubstituted aryl($C_1$-$C_{12}$ alkylene); and R⁶ and R⁷ are independently hydrogen, oxygen, or $C_1$-$C_4$ alkyl.

The term "substituted" as used with respect to formula (3) includes, but is not limited to, substitution with any one or any combination of the following substituents: halogens, hydroxide, $C_1$-$C_4$ alkyl, and $C_1$-$C_4$ alkoxy.

Other suitable delivery agents include those having the following structure and pharmaceutically acceptable salts thereof:

Formula (4)

[Chemical structure: benzene ring with substituents R$^1$, R$^2$, R$^3$, R$^4$, R$^5$, and —O—R$^6$—R$^7$]

wherein (a) R$^1$, R$^2$, R$^3$, and R$^4$ are independently H, —OH, halogen, C$_1$-C$_4$ alkyl, C$_1$-C$_4$ alkenyl, C$_1$-C$_4$ alkoxy, —C(O)R$^8$, —NO$_2$, —NR$^9$R$^{10}$, or —N$^+$R$^9$R$^{10}$R$^{11}$(Y$^-$);

R$^8$ is hydrogen, —OH, C$_1$-C$_6$ alkyl, C$_1$-C$_4$ alkyl substituted with halogen or —OH, C$_2$-C$_4$ alkenyl unsubstituted or substituted with halogen or —OH, or —NR$^{14}$R$^{15}$;

R$^9$, R$^{10}$, and R$^{11}$ are independently hydrogen, oxygen, C$_1$-C$_4$ alkyl unsubstituted or substituted with halogen or —OH, C$_2$-C$_4$ alkenyl unsubstituted or substituted with halogen or —OH;

Y is halide, hydroxide, sulfate, nitrate, phosphate, alkoxy, perchlorate, tetrafluoroborate, carboxylate, mesylate, fumerate, malonate, succinate, tartrate, acetate, gluconate, maleate;

R$^5$ is H, —OH, —NO$_2$, halogen, CF$_3$, —NR$^{14}$R$^{15}$, —N$^+$R$^{14}$R$^{15}$R$^{16}$(Y$^-$), amide, C$_1$-C$_{12}$ alkoxy, C$_1$-C$_{12}$ alkyl, C$_2$-C$_{12}$ alkenyl, carbamate, carbonate, urea, or C(O)R$^{22}$; R$^5$ is optionally substituted with halogen, —OH, —SH, or —COOH; R$^5$ is optionally interrupted by O, N, S, or —C(O)—;

R$^{14}$, R$^{15}$, and R$^{16}$ are independently H or C$_1$-C$_{10}$ alkyl;

R$^{22}$ is H, C$_1$-C$_6$ alkyl, —OH, —NR$^{14}$R$^{15}$;

R$^6$ is substituted or unsubstituted C$_1$-C$_{16}$ alkylene, C$_2$-C$_{16}$ alkenylene, C$_2$-C$_{16}$ alkynylene, C$_5$-C$_{16}$ arylene, (C$_1$-C$_{16}$ alkyl) arylene or aryl(C$_1$-C$_{16}$ alkylene); R$^6$ is optionally substituted with C$_1$-C$_7$ alkyl or C$_1$-C$_7$ cycloalkyl;

R$^7$ is —NR$^{18}$R$^{19}$ or —N$^+$R$^{18}$R$^{19}$R$^{20}$Y$^-$;

R$^{18}$ and R$^{19}$ are independently hydrogen, oxygen, hydroxy, substituted or unsubstituted C$_1$-C$_{16}$ alkyl, substituted or unsubstituted C$_2$-C$_{16}$ alkenyl, substituted or unsubstituted C$_2$-C$_{16}$ alkynyl, substituted or unsubstituted aryl, substituted or unsubstituted alkylcarbonyl (e.g. substituted or unsubstituted (C$_{1-6}$ alkyl)carbonyl), substituted or unsubstituted arylcarbonyl, substituted or unsubstituted alkanesulfinyl (e.g. substituted or unsubstituted (C$_{1-6}$ alkane)sulfinyl), substituted or unsubstituted arylsulfinyl, substituted or unsubstituted alkanesulfonyl (e.g. substituted or unsubstituted (C$_{1-6}$ alkane)sulfonyl), substituted or unsubstituted arylsulfonyl, substituted or unsubstituted alkoxycarbonyl (e.g. substituted or unsubstituted (C$_{1-6}$ alkoxy)carbonyl), or substituted or unsubstituted aryloxyccarbonyl, or substituted or unsubstituted C$_5$-C$_7$ heterocyclic ring (i.e., 5, 6, or 7-membered heterocyclic ring), wherein the substitutions may be halogen or —OH; and R$^{20}$ is independently hydrogen, substituted or unsubstituted C$_1$-C$_{16}$ alkyl, substituted or unsubstituted C$_2$-C$_{16}$ alkenyl, substituted or unsubstituted C$_2$-C$_{16}$ alkynyl, substituted or unsubstituted aryl, substituted or unsubstituted alkylcarbonyl (e.g. substituted or unsubstituted (C$_{1-6}$ alkyl)carbonyl), substituted or unsubstituted arylcarbonyl, substituted or unsubstituted alkanesulfinyl (e.g. substituted or unsubstituted (C$_{1-6}$ alkane)sulfinyl), substituted or unsubstituted arylsulfinyl, substituted or unsubstituted alkanesulfonyl (e.g. substituted or unsubstituted (C$_{1-6}$ alkane)sulfonyl), substituted or unsubstituted arylsulfonyl, substituted or unsubstituted alkoxycarbonyl (e.g. substituted or unsubstituted (C$_{1-6}$ alkoxy) carbonyl), or substituted or unsubstituted aryloxycarbonyl; or (b) R$^1$-R$^{16}$ and R$^{20}$ are as defined above; and R$^{18}$ and R$^{19}$ combine to form a 5, 6, or 7-membered heterocyclic ring optionally interrupted with an oxo group and unsubstituted or substituted with C$_1$-C$_6$ alkyl, C$_1$-C$_6$ alkoxy, aryl, aryloxy, or carbocyclic ring.

According to one embodiment, R$^7$ is morpholino, morpholinium salt, or diethanolamino.

According to another embodiment, R$^6$ is a C$_1$-C$_{16}$ alkylene and R$^7$ is morpholino or a morpholinium salt. Preferably, R$^6$ is C$_4$-C$_{12}$ alkylene, such as an unsubstituted C$_4$-C$_{12}$ alkylene. More preferably, R$^6$ is C$_4$-C$_{10}$, C$_4$-C$_8$, or C$_6$-C$_8$ alkylene, such as an unsubstituted C$_4$-C$_{10}$, C$_4$-C$_8$, or C$_6$-C$_8$ alkylene. According to one embodiment, one of R$^1$-R$^5$ is hydroxy, for example, R$^1$ can be hydroxy.

According to yet another embodiment, when R$^6$ is a C$_1$-C$_{10}$ alkylene, at most one of R$^2$ and R$^4$ is halogen. According to another embodiment, R$^6$ is a C$_8$-C$_{16}$, C$_9$-C$_{16}$, C$_{10}$-C$_{16}$, or C$_{11}$-C$_{16}$ alkylene. For instance, R$^6$ may be a C$_8$, C$_9$, C$_{10}$, C$_{11}$, or C$_{12}$ alkylene (e.g., a normal C$_8$-C$_{12}$ alkylene). According to yet another embodiment, at most one of R$^1$ and R$^5$ is alkyl.

According to yet another embodiment, R$^1$ is hydroxy and R$^2$, R$^3$, R$^4$, and R$^5$ are independently hydrogen or halogen.

According to yet another embodiment, R$^2$ is hydroxy and R$^1$, R$^3$, R$^4$, and R$^5$ are independently hydrogen or halogen.

According to yet another embodiment, R$^3$ is hydroxy and R$^1$, R$^2$, R$^4$, and R$^5$ are independently hydrogen or halogen.

In a preferred embodiment, halogen is F, Cl or Br, more preferably F or Cl, and even more preferably Cl.

According to yet another embodiment, R$^6$ is C$_1$-C$_{16}$ alkylene, (C$_1$-C$_{16}$ alkyl) arylene or aryl(C$_1$-C$_{16}$ alkylene). More preferably R$^6$ is C$_1$-C$_{12}$ alkylene, more preferably C$_3$-C$_{10}$ alkylene, more preferably C$_4$-C$_{10}$ or C$_4$-C$_8$ alkylene, and more preferably C$_6$-C$_8$ alkylene. More preferably, R$^6$ is unsubstituted.

According to yet another embodiment, R$^7$ is —NR$^{18}$R$^{19}$ and R$^{18}$ and R$^{19}$ are independently C$_1$-C$_4$ alkyl (e.g., methyl, ethyl, propyl, or butyl) substituted with —OH. In another embodiment, R$^7$ is —NR$^{18}$R$^{19}$ and R$^{18}$ and R$^{19}$ combine to form a six membered heterocyclic ring substituted with an oxo group.

According to one preferred embodiment, R$^1$ is hydrogen; R$^2$, R$^3$, and R$^4$ are independently hydrogen, halogen, —OH, or —OCH$_3$; R$^5$ is hydrogen, —OH, or —C(O)CH$_3$; R$^6$ is C$_1$-C$_{12}$ alkylene, and R$^7$ is NR$^{18}$R$^{19}$ wherein R$^{18}$ and R$^{19}$ combine to form a 5, 6, or 7 membered heterocyclic ring.

According to another preferred embodiment, one of R$^3$, R$^4$, and R$^5$ is hydroxy and the others are independently halogen or hydrogen; R$^1$ and R$^2$ are independently halogen or hydrogen; R$^6$ is C$_1$-C$_{16}$ alkylene; and R$^7$ is NR$^{18}$R$^{19}$ wherein R$^{18}$ and R$^{19}$ combine to form a 5, 6, or 7 membered heterocyclic ring. R$^6$ is preferably C$_6$-C$_{16}$, C$_6$-C$_{10}$, C$_8$-C$_{16}$, C$_{10}$-C$_{16}$, or C$_4$-C$_8$ alkylene, such as unsubstituted C$_6$-C$_{16}$, C$_6$-C$_{10}$, C$_8$-C$_{16}$, C$_{10}$-C$_{16}$, or C$_4$-C$_8$ alkylene. Preferably, R$^{18}$ and R$^{19}$ form a morpholino or imidazole.

In another preferred embodiment, R$^1$ is hydrogen; R$^2$, R$^3$, and R$^4$ are independently hydrogen, halogen, —OH, or —OCH$_3$; R$^5$ is hydrogen, —OH, or —C(O)CH$_3$; R$^6$ is C$_1$-C$_{12}$ alkylene; and R$^7$ is N$^+$R$^{18}$R$^{19}$R$^{20}$ (Y$^-$) wherein R$^{18}$ and R$^{19}$ are hydroxy substituted C$_1$-C$_{16}$ alkyl and R$^{20}$ is hydrogen.

In another preferred embodiment, R$^1$ is hydrogen; R$^2$, R$^3$, and R$^4$ are independently hydrogen, halogen, —OH, or —OCH$_3$; R$^5$ is hydrogen, —OH, or —C(O)CH$_3$; R$^6$ is C$_1$-C$_{12}$ alkylene; and $R^7$ is $N^+R^{18}R^{19}R^{20}$ $(Y^-)$ wherein $R^{18}$ and $R^{19}$ are hydroxy substituted $C_1$-$C_{16}$ alkyl and $R^{20}$ is hydrogen.

In another preferred embodiment, $R^1$, $R^2$, $R^4$, $R^5$ are independently halogen or hydrogen; $R^3$ is —OH, or —OCH$_3$; and $R^7$ is $N^+R^{18}R^{19}R^{20}$ $(Y^-)$ wherein $R^{18}$ and $R^{19}$ are hydroxy substituted $C_1$-$C_{16}$ alkyl and $R^{20}$ is hydrogen.

According to one preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_6$ alkylene or aryl substituted $C_1$-$C_{12}$ alkyl; and $R^7$ is —NR$^{18}$R$^{19}$ wherein $R^{18}$ and $R^{19}$ combine to form a 5, 6, or 7 membered heterocyclic ring or $N^+R^{18}R^{19}R^{20}$ $(Y^-)$ wherein $R^{18}$ and $R^{19}$ are hydroxy substituted $C_1$-$C_{16}$ alkyl and $R^{20}$ is hydrogen.

In another preferred embodiment, the citrate salt of the delivery agent is used.

Other suitable delivery agents include those having the following structure and pharmaceutically acceptable salts thereof:

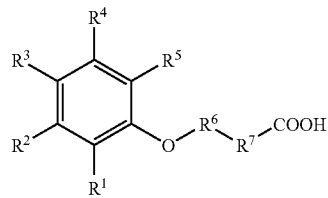

Formula (5)

wherein $R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)R$^8$, —NO$_2$, —NR$^9$R$^{10}$, or —N$^+$R$^9$R$^{10}$R$^{11}$ (R$^{12}$)$^-$;

$R^5$ is H, —OH, —NO$_2$, halogen, —CF$_3$, —NR$^{14}$R$^{15}$, —N$^+$R$^{14}$R$^{15}$R$^{16}$ (R$^{13}$)$^-$, amide, $C_1$-$C_{12}$ alkoxy, $C_1$-$C_{12}$ alkyl, $C_2$-$C_{12}$ alkenyl, carbamate, carbonate, urea, or —C(O)R$^{18}$;

$R^5$ is optionally substituted with halogen, —OH, —SH, or —COOH;

$R^5$ is optionally interrupted by O, N, S, or —C(O)—;

$R^6$ is a $C_1$-$C_{12}$ alkylene, $C_2$-$C_{12}$ alkenylene, or arylene;

$R^6$ is optionally substituted with a $C_1$-$C_4$ alkyl, $C_2$-$C_4$ alkenyl, $C_1$-$C_4$ alkoxy, —OH, —SH, halogen, —NH$_2$, or —CO$_2$R$^8$;

$R^6$ is optionally interrupted by O or N;

$R^7$ is a bond or arylene;

$R^7$ is optionally substituted with —OH, halogen, —C(O)CH$_3$, —NR$^{10}$R$^{11}$, or —N$^+$R$^{10}$R$^{11}$R$^{12}$ (R$^{13}$)$^-$;

$R^8$ is H, $C_1$-$C_4$ alkyl, $C_2$-$C_4$ alkenyl, or —NH$_2$;

$R^9$, $R^{10}$, $R^{11}$, and $R^{12}$ independently H or $C_1$-$C_{10}$ alkyl;

$R^{13}$ is a halide, hydroxide, sulfate, tetrafluoroborate, or phosphate; and $R^{14}$, $R^{15}$ and $R^{16}$ are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, —C(O)R$^{17}$;

$R^{17}$ is —OH, $C_1$-$C_{10}$ alkyl, or $C_2$-$C_{12}$ alkenyl; and $R^{18}$ is H, $C_1$-$C_6$ alkyl, —OH, —NR$^{14}$R$^{15}$, or N$^+$R$^{14}$R$^{15}$R$^{16}$ (R$^{13}$).

According one embodiment, (1) when $R^1$, $R^2$, $R^3$, $R^4$, and $R^5$ are H, and $R^7$ is a bond then $R^6$ is not a $C_1$-$C_6$, $C_9$ or $C_{10}$ alkyl;

(2) when $R^1$, $R^2$, $R^3$, and $R^4$ are H, $R^5$ is —OH, $R^7$ is a bond then $R^6$ is not a $C_1$-$C_3$ alkyl;

(3) when at least one of $R^1$, $R^2$, $R^3$, and $R^4$ is not H, $R^5$ is —OH, $R^7$ is a bond, then $R^6$ is not a $C_1$-$C_4$ alkyl;

(4) when $R^1$, $R^2$, and $R^3$ are H, $R^4$ is —OCH$_3$, $R^5$ is —C(O)CH$_3$, and $R^6$ is a bond then $R^7$ is not a $C_3$ alkyl; and (5) when $R^1$, $R^2$, $R^4$, and $R^5$ are H, $R^3$ is —OH, and $R^7$ is a bond then $R^6$ is not a methyl.

According one preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_{12}$ alkylene, and $R^7$ is a bond or para-phenylene. $R^7$ is more preferably a $C_7$-$C_9$ alkyl.

According to another preferred embodiment, at least one of $R^1$, $R^2$, $R^3$, and $R^4$ is hydrogen, —C(O)CH$_3$, —OH, Cl, —OCH$_3$, F, or —NO$_2$. In one more preferred embodiment, $R^2$ is —C(O)CH$_3$, —OH, —OCH$_3$, or —Cl. In another more preferred embodiment, $R^3$ is Cl, —OCH$_3$, F, or —OH. In yet another more preferred embodiment, $R^4$ is —OCH$_3$ or —NO$_2$.

According to yet another preferred embodiment, $R^5$ is —C(O)CH$_3$, —OH, H, —CH═CHCH$_3$, —NH$_2$, —NO$_2$, —NHC(O)CH$_3$, —CH═CHCO$_2$H, —C(O)CH$_2$CH$_3$, —C(O)NH$_2$, —C(O)NHCH$_3$, —COOH, —C(O)NHCH$_2$CH$_3$, —C(O)NHCH(CH$_3$)$_2$, —OCH$_3$, —C(CH$_3$)$_2$OH, —C(OH)(CH$_3$)$_2$, or —CH(OH)CH$_3$.

According to yet another preferred embodiment, $R^6$ is a linear $C_1$-$C_{12}$ alkylene. More preferably, $R^6$ is —(CH$_2$)$_n$—, where n is an integer from 1 to 10.

According to yet another preferred embodiment, $R^4$ and $R^5$ are not alkyl or halogen.

According to yet another preferred embodiment, $R^7$ is para-phenylene or a bond.

According to yet another preferred embodiment, $R^6$ is —CH$_2$— and $R^7$ is phenylene and, more preferably para-phenylene. More preferably, at least one of $R^1$, $R^2$, $R^3$, and $R^4$ is hydrogen. More preferably, $R^5$ is —C(O)CH$_3$, —OH or —C(CH$_3$)$_2$OH.

According to yet another preferred embodiment, $R^7$ is a bond, $R^5$ is —OH, and $R^1$, $R^2$, $R^3$, and $R^4$ are hydrogen. $R^6$ is preferably $C_4$-$C_{12}$ alkylene and, more preferably, $C_4$-$C_9$ alkylene.

According to yet another preferred embodiment, $R^7$ is a bond, $R^5$ is —OH, and at least one of $R^1$, $R^2$, $R^3$, and $R^4$ is not hydrogen. $R^6$ is preferably $C_1$-$C_{12}$ alkylene, more preferably $C_5$-$C_{12}$ alkylene, and most preferably $C_5$-$C_9$ alkylene.

According to yet another preferred embodiment, $R^7$ is a bond, $R^5$ is —C(O)CH$_3$, and $R^1$, $R^2$, $R^3$, and $R^4$ are hydrogen. $R^6$ is preferably $C_1$-$C_{12}$ alkylene, more preferably $C_3$-$C_{12}$ alkylene, and most preferably $C_3$-$C_7$ alkylene.

According to yet another preferred embodiment, $R^7$ is a bond and $R^1$, $R^2$, $R^3$, $R^4$ and $R^5$ are hydrogen. Preferably, $R^6$ is $C_7$-$C_8$ alkylene.

According to yet another preferred embodiment, $R^7$ is a bond, $R^5$ is hydrogen, and at least one $R^1$, $R^2$, $R^3$, and $R^4$ are not hydrogen. $R^6$ is preferably $C_1$-$C_{12}$ alkylene, more preferably $C_4$-$C_9$ alkylene, and most preferably $C_7$-$C_8$ alkylene.

According to yet another preferred embodiment, $R^2$ is —OH. More preferably, $R^7$ is a bond and $R^5$ is hydrogen. Preferably, $R^6$ is $C_1$-$C_{12}$ alkylene, more preferably $C_3$-$C_9$ alkylene, and most preferably $C_7$ alkylene.

According to yet another preferred embodiment, $R^3$ is —OH. More preferably, $R^7$ is a bond and $R^5$ is hydrogen. $R^6$ is preferably $C_1$-$C_{12}$ alkylene, more preferably $C_3$-$C_9$ alkylene, and most preferably $C_7$ alkylene.

Other suitable delivery agents include those having the following structure and pharmaceutically acceptable salts thereof:

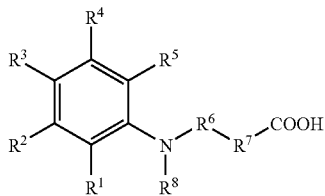

Formula (6)

wherein $R^1$, $R^2$, $R^3$, and $R^4$ are independently H, —OH, halogen, —OCH$_3$, —NR$^{10}$R$^{11}$ or —N$^+$R$^{10}$R$^{11}$R$^{12}$ (R$^{13}$)$^-$;

$R^5$ is H, —OH, —NO$_2$, —NR$^{14}$R$^{15}$, —N$^+$R$^{14}$R$^{15}$R$^{16}$ (R$^{13}$)$^-$, amide, C$_1$-C$_{12}$ alkoxy, C$_1$-C$_{12}$ alkyl, C$_2$-C$_{12}$ alkenyl, carbamate, carbonate, urea, or —C(O)R$^{18}$;

$R^5$ is optionally substituted with —OH, —SH, or —COOH;

$R^5$ is optionally interrupted by O, N, S, or —C(O)—;

$R^6$ is a C$_1$-C$_{12}$ alkylene, C$_1$-C$_{12}$ alkenylene, or arylene;

$R^6$ is optionally substituted with a C$_1$-C$_4$ alkyl, C$_2$-C$_4$ alkenyl, C$_1$-C$_4$ alkoxy, —OH, —SH, halogen, —NH$_2$, or —CO$_2$R$^9$;

$R^6$ is optionally interrupted by O or N;

$R^7$ is a bond or arylene;

$R^7$ is optionally substituted with —OH, halogen, —C(O)CH$_3$, —NR$^{10}$R$^{11}$ or —N$^+$R$^{10}$R$^{11}$R$^{12}$ (R$^{13}$)$^-$;

$R^8$ is H or C$_1$-C$_4$ alkyl;

$R^9$ is H, C$_1$-C$_4$ alkyl, or C$_2$-C$_4$ alkenyl;

$R^{10}$, $R^{11}$, and $R^{12}$ are independently H or C$_1$-C$_{10}$ alkyl;

$R^{13}$ is a halide, hydroxide, sulfate, tetrafluoroborate, or phosphate;

$R^{14}$, $R^{15}$, and $R^{16}$ are independently H, C$_1$-C$_{10}$ alkyl, C$_2$-C$_{12}$ alkenyl, O, or —C(O)R$^{17}$;

$R^{17}$ is —OH, C$_1$-C$_{10}$ alkyl, or C$_2$-C$_{12}$ alkenyl; and $R^{18}$ is —OH, C$_1$-C$_6$ alkyl, —NR$^{14}$R$^{15}$, —N$^+$R$^{14}$R$^{15}$R$^{16}$ (R$^{13}$)$^-$.

According to one embodiment, when $R^5$ is OCH$_3$ then $R^6$ is C$_1$-C$_8$ or C$_{10}$-C$_{12}$ alkyl.

According to a preferred embodiment, $R^5$ is not —OCH$_3$. More preferably, $R^5$ is not alkoxy.

According to another preferred embodiment, $R^1$, $R^2$, $R^3$, and $R^4$ are hydrogen, $R^5$ is —COOH, —C(O)NH$_2$, —C(O)CH$_3$, or —NO$_2$, $R^6$ is —(CH$_2$)$_7$—, and $R^7$ is a bond.

According to yet another preferred embodiment, $R^1$, $R^2$, $R^3$, and $R^4$ are hydrogen, $R^5$ is —C(O)NH$_2$, $R^6$ is —CH$_2$—, and $R^7$ is a para-phenylene.

According to one embodiment, the delivery agents of formula (6) have the formula:

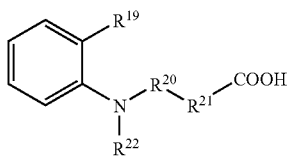

Formula (7)

wherein $R^{19}$ is —NO$_2$ or —C(O)R$^{23}$;

$R^{20}$ is a C$_1$-C$_{12}$ alkylene or C$_1$-C$_{12}$ alkenylene;

$R^{21}$ is a bond or arylene;

$R^{22}$ is H or C$_1$-C$_4$ alkyl; and $R^{23}$ is —OH, C$_1$-C$_6$ alkyl, or —NH$_2$.

Preferred delivery agents include, but are not limited to, SNAC, SNAD, 8-(N-2-hydroxy-5-chlorobenzoyl)aminocaprylic acid, 8-(N-2-hydroxy-4-methoxybenzoyl)-amino-caprylic acid, 4-CNAB, and pharmaceutically acceptable salts thereof.

According to one preferred embodiment, the delivery agent is SNAC or a pharmaceutically acceptable salt thereof. In one embodiment, the delivery agent is a sodium salt of SNAC. In another embodiment, the delivery agent is the monosodium salt of SNAC and can be, for example, any of the polymorphic forms of monosodium SNAC disclosed in U.S. Provisional Application No. 60/569,476, filed May 6, 2004, and U.S. Provisional Application No. 60/619,418, filed Oct. 15, 2004, both of which are hereby incorporated by reference. In yet another embodiment, the delivery agent is the disodium salt of SNAC.

According to another preferred embodiment, the delivery agent is SNAD or a pharmaceutically acceptable salt thereof. In one embodiment, the delivery agent is a sodium salt of SNAD. In another embodiment, the delivery agent is the disodium salt of SNAD.

According to yet another preferred embodiment, the delivery agent is 4-CNAB or a pharmaceutically acceptable salt thereof. In one embodiment, the delivery agent is a sodium salt of 4-CNAB. The sodium 4-CNAB can be any of the amorphous and polymorphic forms described in International Publication No. WO 03/057650, which is hereby incorporated by reference.

Other suitable delivery agents of the present invention are described in U.S. Pat. Nos. 6,699,467, 6,663,898, 6,693,208, 6,693,073, 6,693,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 6,100,298, 6,100,285, 6,099,856, 6,090,958, 6,084,112, 6,071,510, 6,060,513, 6,051,561, 6,051,258, 6,001,347, 5,990,166, 5,989,539, 5,976,569, 5,972,387, 5,965,121, 5,962,710, 5,958,451, 5,955,503, 5,939,381, 5,935,601, 5,879,681, 5,876,710, 5,866,536, 5,863,944, 5,840,340, 5,824,345, 5,820,881, 5,811,127, 5,804,688, 5,792,451, 5,776,888, 5,773,647, 5,766,633, 5,750,147, 5,714,167, 5,709,861, 5,693,338, 5,667,806, 5,650,386, 5,643,957, 5,629,020, 5,601,846, 5,578,323, 5,541,155, 5,540,939, 5,451,410, 5,447,728, 5,443,841, and 5,401,516. Delivery agents of the present invention are also described in U.S. Published Application Nos. 20040110839, 20040106825, 20040068013, 20040062773, 20040022856, 20030235612, 20030232085, 20030225300, 20030198658, 20030133953, 20030078302, 20030072740, 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, and 20010003001. Delivery agents of the present invention are also described in International Publication Nos. WO 2004/410-4018, WO 2004080401, WO 2004062587, WO 2003/057650, WO 2003/057170, WO 2003/045331, WO 2003/045306, WO 2003/026582, WO 2002/100338, WO 2002/070438, WO 2002/069937, WO 02/20466, WO 02/19969, WO 02/16309, WO 02/15959, WO 02/02509, WO 01/92206, WO 01/70219, WO 01/51454, WO 01/44199, WO 01/34114, WO 01/32596, WO 01/32130, WO 00/07979, WO 00/06534, WO 00/06184, WO 00/59863, WO 00/59480, WO 00/50386, WO 00/48589, WO 00/47188, WO 00/46182, WO 00/40203, WO 99/16427, WO 98/50341, WO 98/49135, WO 98/34632, WO 98/25589, WO 98/21951, WO 97/47288, WO 97/31938, WO 97/10197, WO 96/40076, WO 96/40070, WO 96/39835, WO 96/33699, WO 96/30036, WO 96/21464, WO 96/12475, and WO 9612474. Each of the above listed U.S. patents and U.S. and International published applications are herein incorporated by reference.

The delivery agent compounds depicted as carboxylic acids may be in the form of the carboxylic acid or salts thereof. Suitable salts include, but are not limited to, organic and inorganic salts, for example alkali-metal salts, such as sodium (e.g., monosodium and disodium salts), potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

The delivery agent compounds depicted as amines may be in the form of the free amine or salts thereof. Suitable salts include, but are not limited to, organic and inorganic salts, for example sodium salts, sulfate salts, hydrochloride salts, phosphate salts, fluoride salts, carbonate salts, tartrate salts, oxalates, oxides, formates, acetate or citrate.

Salts of the delivery agent compounds of the present invention may be prepared by methods known in the art. For example, sodium salts may be prepared by dissolving the delivery agent compound in ethanol and adding aqueous sodium hydroxide.

Where the delivery agent has an amine moiety and a carboxylic acid moiety, poly amino acids and peptides comprising one or more of these compounds may be used. An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids. One or more of the amino acids or peptide units may be acylated or sulfonated.

The delivery agent may contain a polymer conjugated to it such as described in International Publication No. WO 03/045306. For example, the delivery agent and polymer may be conjugated by a linkage group selected from the group consisting of —NHC(O)NH—, —C(O)NH—, —NHC(O), —OOC—, —COO—, —NHC(O)O—, —OC(O)NH—, —CH$_2$NH—NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly (oxyethylene); poly (propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

The compounds described herein may be derived from amino acids and can be readily prepared from amino acids by methods within the skill of those in the art, such as those described in International Publication Nos. WO96/30036, WO97/36480, WO00/06534, WO00/46812, WO00/50386, WO00/59863, WO 01/32596, and WO 00/07979 and U.S. Pat. Nos. 5,643,957, 5,650,386, and 5,866,536, all of which are incorporated by reference. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art. With regard to protecting groups, reference is made to T. W. Greene, *Protecting Groups in Organic Synthesis*, Wiley, New York (1981), the disclosure of which is hereby incorporated herein by reference.

The delivery agent compound may be purified by recrystallization or by fractionation on one or more solid chromatographic supports, alone or linked in tandem. Suitable recrystallization solvent systems include, but are not limited to, acetonitrile, methanol, ethanol, ethyl acetate, heptane, water, tetrahydrofuran, and combinations thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Gallium Salts and Complexes

Gallium salts which may be employed are those which are pharmaceutically acceptable including nitrate, maltolate, citrate, halide (preferably chloride), carbonate, acetate, tartrate, oxalate, oxide and hydrated oxide as well as those described in U.S. Pat. Nos. 4,529,593, and 4,704,277, which are hereby incorporated by reference. Generally, these gallium salts are non-radioactive. Preferred gallium salts include, but are not limited to, gallium chloride and gallium nitrate and hydrates thereof, such as gallium nitrate nonahydrate.

Gallium complexes which may be employed include those described in U.S. Pat. Nos. 5,258,376, 5,574,027, 5,883,088, 5,968,922, 5,981,518, 5,998,397, 6,004,951, 6,048,851, and 6,087,354, as well as those described in Finnegan et al. Inorganic Chemistry, 26:2171-2176 (1987) and Farrar et al., Food and Chemical Toxicology, 26:523-525 (1988). Each of these references are hereby incorporated by reference. For example, gallium chelates and complexes of 3-hydroxy-4-pyrones (such as a complex of maltol) may be used.

In one embodiment, the gallium complex in the pharmaceutical formulation is a neutral 3:1 (hydroxypyrone:gallium) complex, in which the hydroxypyrone is either an unsubstituted 3-hydroxy-4-pyrone (pyromeconic acid) or a 3-hydroxy-4-pyrone substituted with one to three lower alkyl substitutents (including methyl, ethyl, isopropyl, and n-propyl groups). In a still further embodiment, the 3-hydroxy-4-pyrone is 3-hydroxy-4-pyrone, 3-hydroxy-2-methyl-4-pyrone, 3-hydroxy-2-ethyl-4-pyrone, and 3-hydroxy-6-methyl-4-pyrone. The amount of the hydroxypyrone:gallium complex in the dosage form can be, for example, 0.9 to 1800 mg or 9 to 360 mg.

In another embodiment, the gallium complex in the pharmaceutical formulation is a neutral 3:1 (hydroxypyrone:gallium) complex, and the hydroxypyrone has the formula:

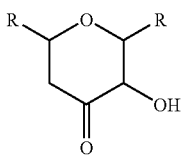

wherein each R is independently selected from hydrogen and alkyl of from 1 to 6 carbon atoms. In a still further embodiment, R is acyclic and unbranched. The hydroxypyrone in the gallium complex can be, for example, maltol or pyromeconic acid. According to one embodiment, the complex is gallium maltolate (tris(3-hydroxy-2-methyl-4H-pyran-4-onato)gallium). See Bernstein et al., "Chemistry and Pharmacokinetics of Gallium Maltolate. A Compound With High Oral Gallium Bioavailability", *Metal-Based Drugs* 7(1):33-47 (2000), which is hereby incorporated by reference.

The aforementioned gallium hydroxypryone complex can be administered with a pharmaceutically compatible buffering agent to raise the pH of the stomach fluids to about 5-9, and preferably to about 6-7. Examples of such buffering agents include, but are not limited to, calcium carbonate ($CaCO_3$), and sodium bicarbonate ($NaHCO_3$). In one embodiment, the gallium complex is administered with calcium carbonate, sodium bicarbonate, and/or an excess of free hydroxypyrone (or a salt thereof containing a physiologically acceptable cation). The weight ratio of free hydroxypyrone to gallium complex preferably ranges from 0.1 to 100. In one embodiment, the gallium complex is administered in a delayed release form with or without calcium carbonate, sodium bicarbonate, and/or an excess of free hydroxypyrone (or a salt thereof containing a physiologically acceptable cation). The buffering agent and/or free hydroxypyrone can be included in the pharmaceutical formulation of the present invention, or administered concurrently therewith.

In another embodiment, gallium is administered as a complex having the formula:

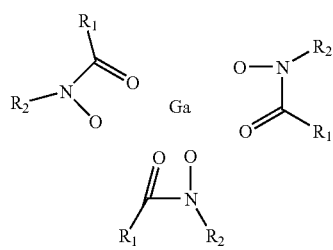

wherein each occurrence of $R_1$ is a $C_1$-$C_8$ n-alkyl and each occurrence of $R_2$ is H or $C_1$-$C_2$ alkyl, or $R_1$ and $R_2$ together from tetra or penta-methylene. See U.S. Pat. No. 5,196,412, which is hereby incorporated by reference.

According to another embodiment, the pharmaceutical formulation includes from about 0.01, 0.1, or 0.5 to about 1, 5, 10, or 20 grams of gallium salt. According to yet another embodiment, the pharmaceutical formulation includes a sufficient amount of gallium salt to provide, upon ingestion to a human, from about 10 to about 400 or 1400 mg/m²/day or more preferably 100-300 mg/m²/day. According to yet another embodiment, the pharmaceutical formulation includes a sufficient amount of gallium salt to provide, upon ingestion to a human, one or more of the following:

(a) plasma gallium concentrations of about 0.1 to about 5 μg/ml or about 0.9 to about 2.0 μg/ml, (b) average steady state plasma levels of gallium from about 1000 to about 2500 ng/ml, or (c) a decrease in serum calcium (corrected for albumin) of at least 2.0 mg/dl in a human with hypercalcemia (such as cancer-related hypercalcemia).

Delivery Systems

The pharmaceutical formulations may be in the form of a liquid or solid. Liquid formulations may be water-based. Dosing solutions may be prepared by mixing a solution of the delivery agent with a solution of the gallium salt prior to administration. Alternately, a solution of the delivery agent (or gallium salt) may be mixed with the solid form of the gallium salt (or delivery agent). The delivery agent and the gallium salt may also be mixed as dry powders and then dissolved in solution. Stabilizing additives may be incorporated into the solution, at, for example, a concentration ranging between about 0.1 and 20% (w/v). The solution may also include a pharmaceutically acceptable carrier, such as phosphate buffered saline and citrate buffers. Other suitable additives include sodium chloride and dextrose.

Solid pharmaceutical formulations may be in the form of tablets, capsules (including hard and soft gelatin capsules), and particles, such as powders and sachets. Solid dosage forms may be prepared by mixing the solid form of the delivery agent with the solid form of the gallium salt. Alternately, a solid may be obtained from a solution of delivery agent and gallium salt by methods known in the art, such as freeze-drying (lyophilization), precipitation, crystallization and solid dispersion.

The pharmaceutical formulations of the present invention can also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The pharmaceutical formulations can include any one or combination of excipients, diluents, disintegrants, lubricants, fillers, plasticizers, colorants, flavorants, taste-masking agents, sugars, sweeteners, salts, and dosing vehicles, including, but not limited to, water, 1,2-propane diol, ethanol, olive oil, or any combination thereof.

The amount of gallium salt (e.g., gallium nitrate) included in the pharmaceutical formulation is an amount effective to accomplish the purpose of the gallium containing salt for the target indication. The amount of gallium salt in the pharmaceutical formulation typically is a pharmacologically, biologically, therapeutically, or chemically effective amount. However, the amount can be less than that amount when the pharmaceutical formulation is used in a dosage unit form of the present invention because the dosage unit form may contain a plurality of delivery agent/gallium salt pharmaceutical formulations or may contain a divided pharmacologically, biologically, therapeutically, or chemically effective amount. The total effective amount can then be administered in cumulative units containing, in total, an effective amount of the gallium salt.

The total amount of gallium salt to be used can be determined by methods known to those skilled in the art. However, because the pharmaceutical formulations of the invention may deliver gallium salt more efficiently than formulations containing the gallium salt alone, lower amounts of gallium salt than those used in prior dosage unit forms or delivery systems can be administered to the subject, while still achieving the same blood levels and therapeutic effects.

The delivery agents facilitate the delivery of gallium salt, particularly in oral form, but are also be useful in intranasal, sublingual, intraduodenal, subcutaneous, buccal, intracolonic, rectal, vaginal, mucosal, pulmonary, transdermal, intradermal, parenteral, intravenous, intramuscular and ocular systems.

The pharmaceutical formulation can be a sustained release oral pharmaceutical formulation which provides for controlled, modified, delayed and/or sustained release of the gallium salt. Such formulations can be prepared by methods known in the art.

The pharmaceutical formulations are useful for administering gallium salts to mammals including, but not limited to, horses, rodents, cows, pigs, dogs, cats, primates, and particularly humans.

According to another embodiment the pharmaceutical formulation includes other medications which treat, cure, mitigate or prevent hypercalcemia, malignancies, or other indications for which gallium is effective. For example, in one embodiment, the pharmaceutical composition includes a chemotherapeutic agent. In another embodiment, the pharmaceutical composition includes an adjunctive chemotherapeutic agent. The pharmaceutical formulation of the present invention may be administered during or subsequent to chemotherapy. According to one preferred embodiment, when the pharmaceutical formulation is to be administered subsequent to chemotherapy, the pharmaceutical formulation includes an adjunctive chemotherapeutic agent, such as filgrastim or erythropoietin.

Methods of Treatment

The pharmaceutical formulation of the present invention can be administered to treat and/or prevent any disorder for which gallium salts are known to be capable of treating and/or preventing. Typically, an effective amount of the pharmaceutical formulation is administered to treat and/or prevent the desired disorder. Such disorders include, but are not limited to, hypercalcemia (including cancer-related hypercalcemia and hypercalcemia associated with malignancies, including non-small cell lung cancer, breast cancer, prostate cancer, multiple myeloma, squamous cell cancers, kidney cancer, uretral and bladder cancers, and cancers of head and neck), a disorder associated with excessive (or accelerated) loss of calcium from bone, osteopenia, osteoporosis, bone destruction due to metastasis from malignant tumors, hyperparathyroidism, and periodontal disease.

The pharmaceutical formulation can also be administered to:

(1) increase uptake of calcium by bones bone in a mammal (such as a human), inhibit resorption (or release) of calcium from bone in a mammal (such as a human) with hypercalcemia, bone fragility, or other disorders associated with abnormally increased calcium resorption (or release), (2) treat bone pain due to excessive (or accelerated) loss of calcium from bone, and/or (3) prevent bone fractures due to excessive (or accelerated) loss of calcium from bone, (4) treat or prevent Paget's disease, (5) inhibit osteoclastic activity, and/or promote osteoblastic activity, (6) treat or prevent of urethral (urinary tract) malignancies, (7) treat or prevent tumors, (8) treat or prevent cancers, including urethral, small cell lung, genitourinary malignancies such as prostrate, testicular and bladder cancers, lymphoma, leukemia, and multiple myeloma, (9) manage bone metastases (and associated pain),

(10) attenuate immune response, including allogenic transplant rejection,

(11) disrupt iron metabolism,

(12) promote cell migration,

(13) enhance repair and augmentation of skin, and connective and support tissues (e.g. skin, tendon, fascia, collagen-containing tissue than encapsulate tissue, bone), i.e. wound repair,

(14) attenuate, treat, or prevent infectious processes of *Mycobacterium* species, including but not limited to, *Mycobacterium tuberculosis*, and *Mycobacterium avium* complex,

(15) treat skin disorders and blemishes, e.g., facilitate healing of tears, breaks, wrinkles or defects in the skin,

(16) treat AIDS-associated non-Hodgkin's lymphoma (see U.S. Pat. No. 6,562,870),

(17) treat viral infections, e.g. to treat HIV (see U.S. Pat. No. 5,525,598), and

(18) increase bone growth, decrease hydroxyapatite solubility, increase the size and/or the perfection of hydroxyapatite crystals in bone, and/or increase the tensile strength of bone,

(19) increase calcium accretion in bone tissue and/or decrease bone resorption, and

(20) treat or prevent urothelial carcinoma or nonsquamous cell cervical carcinoma (see Bernstein et al., *Metal-Based Drugs* 7(1):33-47 (2000)).

The pharmaceutical formulations can be administered to treat the indications for gallium salts found in (1) the *Physicians' Desk Reference* (58$^{th}$ Ed., 2004, Medical Economics Company, Inc., Montvale, N.J.), (2) Fauci, A S, et. al., *Harrison's Principles of Internal Medicine* (14$^{th}$ Ed., 1998, McGraw-Hill Health Professions Division, New York), and (3) U.S. Pat. Nos. 4,529,593, 4,704,277, 5,196,412, 5,258,376, 5,525,598, 5,556,645, 5,574,027, 5,686,116, 5,883,088, 5,981,518, 5,998,397, 5,968,922, 6,004,951, 6,048,851, 6,087,354, 6,165,514, and 6,562,870. All of the above-mentioned patents and publications are herein incorporated by reference in their entirety.

Cancer-related hypercalcemia can be treated by administration of the pharmaceutical formulation of the present invention containing a relatively high dose of a gallium salt for several days, followed by daily administration of a pharmaceutical formulation containing a lower dose of a gallium salt to prevent recurrence. In the treatment of loss of calcium from bone due to periodontal disease a gallium salt and a delivery agent may be administered topically in an intra-oral formulation comprising, for example, a highly concentrated rinse, gel, or other pharmaceutically acceptable carrier for the local treatment of periodontal disease.

In one embodiment, the treatment of cancer is provided by administration of an effective amount of the pharmaceutical formulation of the present invention. Effective amounts of gallium include dosage amounts and schedules that, when orally administered, correspond to previously-reported administration schedules via intravenous or subcutaneous injection of gallium salts. For example, in one embodiment the oral equivalent of 700-750 mg/m$^2$ of gallium nitrate administered by short infusion is orally administered every 2-3 weeks, or the oral equivalent of 300 μg/m$^2$/day administered by infusion is administered for three consecutive days, to be repeated every 2 weeks; or the oral equivalent of 300 mg/m$^2$/day administered by infusion for 7 consecutive days is orally administered, to be repeated every 3-5 weeks. See e.g. Foster et al., "Gallium Nitrate: The Second Metal With Clinical Activity", Cancer Treatment Reports, 70:1311:1319 (1986), which is hereby incorporated by reference.

In another embodiment, a topical composition comprising a gallium salt (e.g. gallium nitrate) and a delivery agent are applied to the skin to treat skin conditions including, wrinkles due to aging, and skin defects due to prior injury, such as acne or previous trauma. See U.S. Pat. No. 5,556,645, which is hereby incorporated by reference.

In one embodiment, a topical composition comprising a gallium salt (e.g., gallium nitrate) and a delivery agent of the present invention is applied to treat a wound. In a still further embodiment, topical composition of the present invention is incorporated into or applied to a bandage or dressing for a wound. See U.S. Pat. No. 6,165,514, which is hereby incorporated by reference.

The following example illustrates the invention without limitation. All parts are given by weight unless otherwise indicated.

EXAMPLE 1

Gallium Nitrate Oral Delivery

Gallium nitrate (55 mg/kg) with or without the disodium salt of SNAC or disodium salt of compound 2 of International Publication No. WO 03/045306 (8-(2-hydroxyphenoxy)octyldiethanolamine) was administered orally to rodents (n=5) as a solution. Gallium nitrate (5.5 mg/kg) was also administered to rats without a delivery agent by intravenous administration. The plasma gallium concentrations were measured every fifteen minutes up to an hour after administration. The results are shown in FIG. 1.

The above mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. An oral pharmaceutical composition comprising (a) gallium nitrate nonahydrate and (b) a delivery agent selected from N-(8-[2-hydroxybenzoyl]-amino)caprylic acid and pharmaceutically acceptable salts thereof.

2. The oral pharmaceutical composition of claim 1, wherein the delivery agent is a sodium salt of N-(8-[2-hydroxybenzoyl]-amino)caprylic acid.

3. The pharmaceutical composition of claim 1, wherein the pharmaceutical formulation provides sustained release of the gallium nitrate nonahydrate.

4. The pharmaceutical composition of claim 1, wherein the pharmaceutical formulation, upon oral ingestion to a human, provides plasma gallium concentrations of about 0.1 to about 5 µg/ml.

5. The pharmaceutical composition of claim 1, wherein the pharmaceutical composition, upon oral ingestion to a human, provides one or more of the following:
 (a) plasma gallium concentrations of about 0.1 to about 5 µg/ml or about 0.9 to about 2.0 µg/ml,
 (b) average steady state plasma levels of gallium from about 1000 to about 2500 ng/ml, or
 (c) a decrease in serum calcium (corrected for albumin) of at least 2.0 mg/dl in a human with hypercalcemia (such as cancer-related hypercalcemia).

6. The oral pharmaceutical composition of claim 1, wherein the weight ratio of delivery agent to gallium nitrate nonahydrate is about 3.6:1.

7. The oral pharmaceutical composition of claim 1, comprising about 55 mg of gallium nitrate nonahydrate and about 200 mg of a delivery agent selected from N-(8-[2-hydroxybenzoyl]-amino)caprylic acid and pharmaceutically acceptable salts thereof.

8. A method of preparing an oral pharmaceutical composition comprising mixing a delivery agent selected from N-(8-[2-hydroxybenzoyl]-amino)caprylic acid and pharmaceutically acceptable salts thereof, gallium nitrate nonahydrate and, optionally, one or more pharmaceutically acceptable excipients or additives.

9. The method of claim 8, wherein the weight ratio of delivery agent to gallium nitrate nonahydrate is about 3.6:1.

10. The method of claim 8, wherein the oral pharmaceutical composition comprises about 55 mg of gallium nitrate nonahydrate and about 200 mg of a delivery agent selected from N-(8-[2-hydroxybenzoyl]-amino)caprylic acid and pharmaceutically acceptable salts thereof.

11. A method of treating hypercalcemia in a mammal in need thereof comprising orally administering to the mammal an effective amount of the pharmaceutical composition of claim 1.

* * * * *